United States Patent [19]

Monte et al.

[11] Patent Number: 5,693,789

[45] Date of Patent: Dec. 2, 1997

[54] PROCESS FOR THE PREPARATION OF A PROTOPORPHYRIN

[75] Inventors: William T. Monte, Grayslake; Aline C. Lindbeck, Waukegan; Xiu C. Wang, Gurnee; Annette A. Johnston, Highland Park, all of Ill.

[73] Assignee: Abbott Laboratories, Abbott Park, Ill.

[21] Appl. No.: 634,754

[22] Filed: Apr. 10, 1996

[51] Int. Cl.$^6$ .................................................. C07D 487/22
[52] U.S. Cl. ............................................................ 540/145
[58] Field of Search ................................................ 540/145

[56] References Cited

U.S. PATENT DOCUMENTS

| | | | |
|---|---|---|---|
| 4,920,143 | 4/1990 | Levy et al. | 514/410 |
| 5,149,708 | 9/1992 | Dolphin et al. | 514/410 |
| 5,354,858 | 10/1994 | Morgan et al. | 540/145 |

FOREIGN PATENT DOCUMENTS 9404147  3/1994  WIPO.

OTHER PUBLICATIONS

Callot, H. J., et al., "Additions to Porphins Involving the Formation of New Carbon–Carbon Bonds", *J.C.S. Perkin I*, 1424–1427 (1973).

Meunier, I., et al., "Benzoporphyrin Derivatives: Synthesis, Structure and Preliminary Biological Activity", *J. Chem. Soc. Perkin. Trans.*, I:961–969 (1994).

Meunier, I., et al., "New Synthesis Of Benzoporphyrin Derivatives And Analogues For Use In Photodynamic Therapy", *Bioorganic & Medicinal Chemistry Letters*, 2(12):1575–1580 (1992).

Pandey, R.K., et al., "Long Wavelength Photosensitizers Related to Chlorins and Bacteriochlorins for use in Photodynamic Therapy", *J. Chem. Soc. Perkin Trans.*, I:1377–1385 (1992).

Pangka, V.S., et al., "Diels–Alder Reactions of Protoporphyrin IX Dimethyl Ester with Electron–Deficient Alkynes", *J. Org. Chem.*, 51:1094–1100 (1986).

*Primary Examiner*—Mukund J. Shah
*Assistant Examiner*—Pavanaram K. Sripada
*Attorney, Agent, or Firm*—Michael J. Ward

[57] ABSTRACT

The present invention provides a process for the preparation of BPD 1,4-diene diester A-ring comprising reacting hematoporphyrin IX dimethyl ester with dimethyl acetylenedicarboxylate followed by purification of the product by a series of fractional crystallizations.

18 Claims, No Drawings

PROCESS FOR THE PREPARATION OF A PROTOPORPHYRIN

TECHNICAL FIELD

This invention relates to a process useful for the synthesis of organic compounds. More particularly, this invention concerns a method of preparation of intermediates useful for the preparation of benzoporphyrin photodynamic antitumour agents.

BACKGROUND OF THE INVENTION

Trans-(±)-18-ethenyl-4, 4a-dihydro-3, 4-bis (methoxycarbonyl)-4a, 8, 14, 19-tetramethyl-23H, 25H-benzo[b]porphine-9, 13-dipropanoic acid, 9-methyl ester, and trans-(±)-18ethenyl-4, 4a-dihydro-3, 4-bis (methoxycarbonyl)-4a, 8, 14, 29-tetramethyl-23H, 25H-benzo[b]-porphine-9, 13-dipropanoic acid, 13-methyl ester. (BPD-MA) has shown promise as a photodynamic antitumour agent (see Pandey et al, *Proc. SPIE*, (1989) 1065, 164). In order to proceed with further testing and evaluation as a potential drug, it is necessary to develop a process for preparation of BPD-MA in kilogram quantities.

Scheme 1

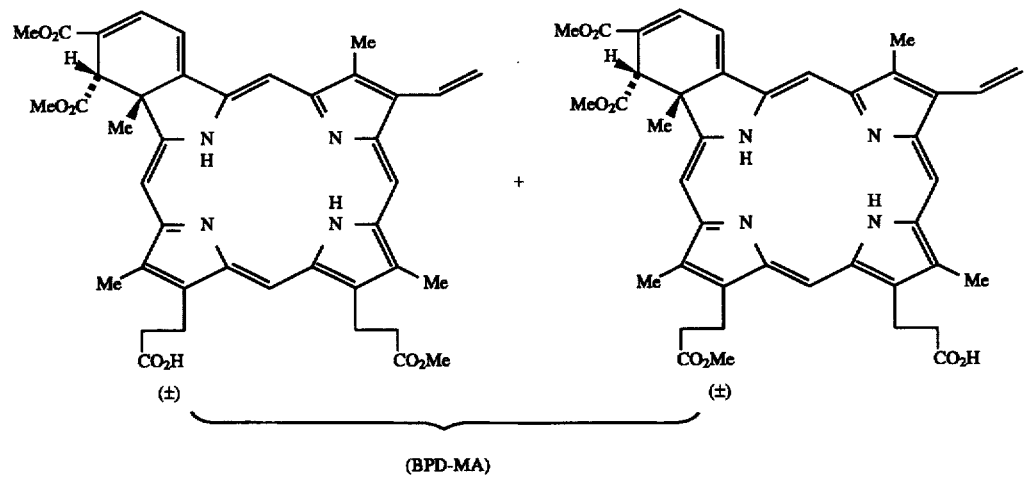

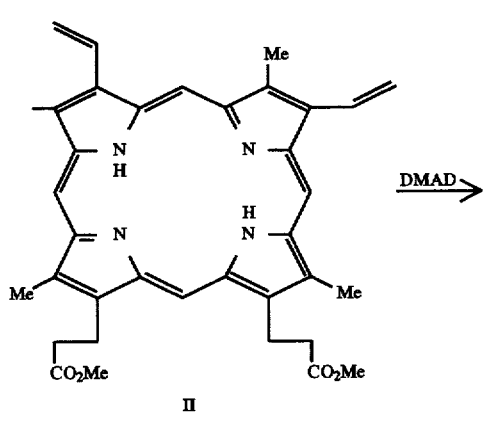

A straightforward preparation of BPD-MA is outlined in Scheme 1. Hematoporphyrin IX dihydrochloride (I) is heated in N,N-dimethylformamide and then is reacted with trimethyl orthoformate and sulfuric acid to give Protoporphyrin IX dimethyl ester (PDE) (II). Diels-Alder reaction of PDE with dimethyl acetylenedicarboxylate (DMAD) gives BPD 1,4-diene diester A-ring (III). Rearrangement of the Diels Alder adduct (III) with base, for example DBU (1,8-diazabicyclo[5.4.0]undec-7-ene) gives the conjugated compound BPD 1,3-diene diester A-ring (IV). Treatment of (IV) with aqueous acid gives the monomethyl ester BPD-MA.

-continued
Scheme 1

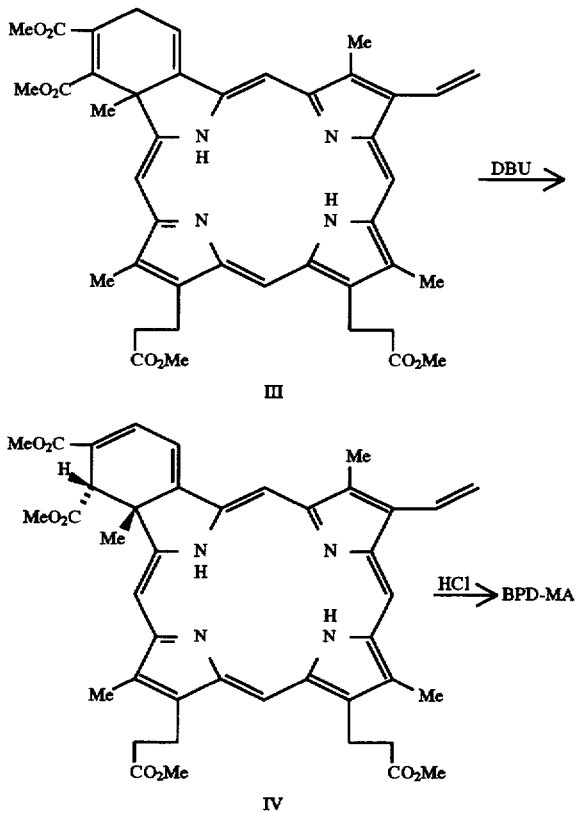

Due to the presence of two possible reaction sites in PDE, the Diels-Alder reaction results in the formation of two isomers; the desired "A-ring" isomer (II), and the "B-ring" isomer resulting from reaction of the other diene, as well as the bis adduct resulting from addition to both dienes. The isomers have been separated by chromatography after the Diels-Alder reaction (see Pangka et al, *J. Org. Chem.*, (1986), 51, 1094), or after the base-catalyzed rearrangement to form III (see Meunier et al, *J. Chem. Soc. Perkin* 1, (1994) 961). Other methods of minimizing the isomer problem include starting with a symmetrical diene instead of PDE (see Pandey et al, *J. Chem. Soc. Perkin* 1, (1992) 1377), or preparing a starting material which contains only a single diene (see Meunier et al, *J. Chem. Soc. Perkin* 1, (1994) 961).

All of the above methods suffer from disadvantages which render them unsuitable for the large-scale preparation of BPD-MA. Chromatographic separations on a kilogram scale require prohibitive quantities of silica gel and solvents, leading to problems of cost and solvent disposal. In addition, the porphyrins are unstable on silica gel resulting in loss of compound during purification. Chemical methods of differentiating between the A and B ring all require additional reactions and purification steps resulting in increased reagent and handling costs.

SUMMARY OF THE INVENTION

The present invention relates to a process for the isolation of BPD 1,4-Diene Diester A-ring from the reaction of protoporphyrin IX dimethyl ester (PDE) with dimethyl acetylenedicarboxylate (DMAD) comprising dissolving the reaction product mixture in a first solvent, adding a second solvent in an amount sufficient to induce precipitation of a solid, separating the solid, dissolving the solid in a third solvent, adding a fourth solvent in an amount sufficient to induce precipitation of a second solid from a mother liquor containing substantially all of the product BPD 1,4-Diene Diester A-ring, separating the mother liquor from the solid, and isolating the product BPD-Diene Diester A-ring from the mother liquor.

DETAILED DESCRIPTION OF THE INVENTION

The present invention relates to a process wherein BPD 1,4-diene diester A-ring is substantially more soluble in a variety of organic solvents than PDE and the undesired B-ring isomer, and can be readily isolated from the Diels-Alder reaction mixture by fractional crystallization. This procedure requires no chromatographic separations or additional chemical reactions and is therefore suitable for use in the pilot plant.

Accordingly, the present invention provides a process for the isolation of BPD 1,4-Diene Diester A-ring from the reaction of protoporphyrin IX dimethyl ester (PDE) with dimethyl acetylenedicarboxylate (DMAD) comprising dissolving the reaction product mixture in a first solvent, adding a second solvent in an amount sufficient to induce precipitation of a solid, separating the solid, dissolving the solid in a third solvent, adding a fourth solvent in an amount sufficient to induce precipitation of a second solid from a mother liquor containing substantially all of the product BPD 1,4-Diene Diester A-ring, separating the mother liquor from the solid, and isolating the product BPD-Diene Diester A-ring from the mother liquor.

In accordance with the foregoing procedure, protoporphyrin IX dimethyl ester (PDE) is reacted with an excess of dimethyl acetylenedicarboxylate (DMAD) with or without an organic solvent such as dichloromethane, dichloroethane, or toluene. The reaction mixture is stirred and optionally heated until product formation ceases. At this point, the reaction mixture comprises BPD 1,4-diene diester A-ring and BPD 1,4-diene diester B-ring, as well as bis adduct, unreacted PDE and DMAD, and polymeric material. The reaction mixture is then concentrated, preferably by vacuum distillation, and the residue is dissolved in a first solvent. Representative first solvents include dichloromethane, ethyl acetate, methanol, ethanol, 1-propanol, 2-propanol, 1-butanol, tetrahydrofuran, N,N-dimethylformamide, acetonitrile, acetone, benzene, toluene, xylene, and the like. The resulting solution is then mixed with an amount of a second solvent sufficient to precipitate all of the porphyrins and polymeric material. Second solvents include ethers such as diethyl ether, methyl t-butyl ether, and the like, and hydrocarbon solvents such as hexane, heptane, octane, cyclohexane, and the like. Typical solvent ratios are about 1 part by volume of first solvent to 5–10 parts by volume of second solvent. The precipitate formed upon addition of the second solvent is then collected, preferably by filtration. Residual DMAD is then removed by washing the solid with a first solvent/second solvent mixture comprising amounts of first and second solvents in about the same ratio as was used to precipitate the porphyrins and polymeric material.

The washed solid, which comprises BPD 1,4-diene diester A-ring and BPD 1,4-diene diester B-ring, bis adduct, PDE, and polymeric material is then dissolved in a third solvent. The mixture may be heated to facilitate dissolution of the solid. Representative third solvents include dichloromethane, ethyl acetate, methanol, ethanol, 1-propanol, 2-propanol, 1-butanol, tetrahydrofuran, N,N-dimethylformamide, acetonitrile, acetone, benzene, toluene, xylene, and the like. To the resulting solution is added an amount of a fourth solvent, usually about 3–5 parts by volume, sufficient to precipitate substantially all of the polymeric material from the solution. Typical fourth solvents include diethyl ether, methyl t-butyl ether, and the like, and hydrocarbon solvents such as hexane, heptane, octane, cyclohexane, and the like. The precipitate and mother liquor are then separated, preferably by filtration, and the mother liquor is concentrated, preferably by vacuum distillation, to give a solid residue comprising BPD 1,4-diene diester A-ring, BPD 1,4-diene diester B-ring, bis adduct, and PDE. The precipitated polymeric material may be optionally washed with a third solvent/fourth solvent mixture comprising amounts of the third and fourth solvents in about the same ration as was used to precipitate the polymeric material, and the washings combined with the mother liquor prior to evaporation.

The solid mixture of BPD 1,4-diene diester A-ring, BPD 1,4-diene diester B-ring, bis adduct, and PDE may then be dissolved in a fifth solvent. The mixture may be heated to facilitate dissolution of the solid. Representative fifth solvents include ethyl acetate, acetone, acetonitrile, methanol, ethanol, 2-propanol, tetrahydrofuran, N,N-dimethylformamide, and the like. To the resulting solution is then added an amount of a sixth solvent, generally 3–5 parts by volume, sufficient to induce crystallization of the BPD 1,4-diene diester B-ring, bis adduct, and PDE while leaving substantially all to the desired BPD 1,4-diene diester A-ring in the mother liquor. Representative sixth solvents include diethyl ether, methyl t-butyl ether, hexane, heptane, octane, cyclohexane, and the like. The mixture may be cooled to facilitate precipitation of all of the undesired compounds. The mother liquor is then evaporated to leave the product BPD 1,4-diene diester A-ring. The collected solids may be optionally washed with a polar solvent/fifth solvent mixture and the washings combined with the mother liquor prior to evaporation of the solvents.

In a preferred embodiment, the first and third solvents are independently selected from the group consisting of benzene, toluene, and xylene; the second, fourth, and sixth solvents are independently selected from the group consisting of hexane, heptane, octane, and cyclohexane; and the polar organic solvent is ethyl acetate.

In yet another preferred embodiment of the present invention, PDE is reacted with excess DMAD in refluxing toluene to form the product mixture described above. The reaction mixture is then distilled to dryness under vacuum and the residue redissolved in toluene. The toluene solution is then added to between 5 and 10 parts by volume of heptane to induce precipitation of a solid. The solid is collected by filtration and washed with a solvent mixture comprising about 1 part by volume toluene and between 5 and 10 parts by volume of heptane. The solid is then dissolved in toluene at a temperature of from about 20° to 60° C. Best results are obtained when the mixture is heated to about 40° to 50° C. The toluene solution is then mixed with a solvent mixture comprising about 1 pan by volume toluene and between 3 to 5 parts by volume of heptane to induce precipitation of a solid from a mother liquor containing substantially all of the product. The mother liquor and solid are separated by filtration and the mother liquor is evaporated by vacuum distillation to leave a solid residue. The last traces of toluene remaining in the solid may be removed by dissolving the solid in ethyl acetate and distilling the solution to dryness. The solid residue is then dissolved in ethyl acetate and the ethyl acetate solution is mixed with about 0.25 to 0.5 parts by volume of heptane to induce precipitation of a solid from a mother liquor containing substantially all of the product. The solid and mother liquor are then separated by filtration. Additional product may be recovered from the solid by washing with a solvent mixture comprising 1 part by volume ethyl acetate and between 3 to 5 parts by volume of heptane. The mother liquor and washings are then combined and evaporated by vacuum distillation to give the product BPD 1,4-diester A-ring.

The foregoing may be better understood by the following Examples, which are presented for purposes of illustration and are not intended to limit the scope of the invention.

EXAMPLE 1

Laboratory-Scale Preparation of BPD 1,4-Diene Diester A-ring.

A mixture of protoporphyrin IX dimethyl ester (50 g) in toluene (2.7 L) was stirred for 30 minutes at ambient temperature. Dimethyl acetylenedicarboxylate (96 g) was added and the reaction mixture was heated for 35 hours at reflux. The reaction mixture was concentrated in vacuo and the residue was dissolved in toluene (500 mL). The toluene solution was added to heptane (4000 mL), and the resulting solid was filtered and washed with toluene/heptane (1:8). The solid was then dissolved in toluene (1000 mL) at 45° C. and the toluene solution was added to a toluene/heptane mixture (1:4, 5000 mL) at 45° C. The resulting suspension was cooled to ambient temperature and filtered. The filtrate was concentrated in vacuo and the residue was dissolved in ethyl acetate (320 mL). To the ethyl acetate solution was added heptane (100 mL) and the mixture was left standing overnight at 2° C. and then at −10° C. for 2 hours. The resulting suspension was filtered and the solid was washed with ethyl acetate/heptane (1:4). The filtrate and washings were combined and concentrated in vacuo to give BPD 1,4-diene diester A-ring (24 g) which was sufficiently pure to be used without further purification.

EXAMPLE 2

Kilogram-Scale Preparation of BPD 1,4-Diene Diester A-ring

To a solution, under $N_2$, of protoporphyrin IX dimethyl ester (5.6 kg) in toluene (306 kg) was added dimethyl acetylenedicarboxylate (11.2 kg) and the mixture was heated at reflux for 35 hours. The reaction mixture was concentrated in vacuo at 45° C, the residue was dissolved in toluene (59 kg), and the toluene solution was added to 367 kg of heptane over 1 hour. The mixture was stirred for 1.5 hours at ambient temperature and filtered. The filter cake was washed with toluene-heptane (1:8 V/V) to remove residual dimethyl acetylenedicarboxylate. The filter cake was then dissolved in toluene (49 kg) at 45° C. A mixture of toluene (101 kg) and heptane (316 kg) was added at 45° C. The mixture was cooled to ambient temperature and filtered. The filtrate was concentrated in vacuo and azeotroped with ethyl acetate. The residue was dissolved in ethyl acetate (27 kg) at ambient temperature and heptane (6.6 kg) was added. The solution was cooled to 0°±10° C. for 5 hours and then filtered. The precipitate was washed with a mixture of ethyl acetate (2 kg) and heptane (6 kg). The filtrate and the wash were combined and concentrated in vacuo at 40° C. The residue was azeotroped with methylene chloride. The product BPD 1,4-Diene Diester A-ring (III) weighed 2.2 kg (34%) and was used for the next step without further purification.

We claim:

1. A process for the isolation of a product containing a compound of formula III from the reaction of protoporphyrin IX dimethyl ester (PDE) with dimethyl acetylenedicarboxylate (DMAD) comprising dissolving the reaction product mixture in a first solvent, adding a second solvent in an amount sufficient to induce precipitation of a solid, separating the solid, dissolving the solid in a third solvent, adding a fourth solvent in an amount sufficient to induce precipitation of a second solid from a mother liquor containing substantially all the product separating the mother liquor from the solid, and isolating the product from the mother liquid.

2. The process of claim 1 wherein the first solvent is selected from the group consisting of dichloromethane, ethyl acetate, methanol, ethanol, 1-propanol, 2-propanol, 1-butanol, tetrahydrofuran, N,N-dimethylformamide, acetonitrile, acetone, benzene, toluene, and xylene.

3. The process of claim 1 wherein the second solvent is selected from the group consisting of diethyl ether, methyl t-butyl ether, hexane, heptane, octane, and cyclohexane.

4. The process of claim 1 wherein the first solvent is selected from the group consisting of benzene, toluene, and xylene.

5. The process of claim 1 wherein the second solvent is selected from the group consisting of hexane, heptane, octane, and cyclohexane.

6. The process of claim 1 wherein the first solvent is toluene and the second solvent is heptane.

7. The process of claim 1 wherein the third solvent is selected from the group consisting of dichloromethane, ethyl acetate, methanol, ethanol, 1-propanol, 2-propanol, 1-butanol, tetrahydrofuran, N,N-dimethylformamide, acetonitrile, acetone, benzene, toluene, and xylene.

8. The process of claim 1 wherein the fourth solvent is selected from the group consisting of diethyl ether, methyl t-butyl ether, hexane, heptane, octane, and cyclohexane.

9. The process of claim 1 wherein the third solvent is toluene and the fourth solvent is heptane.

10. The process of claim 1 further comprising evaporating the mother liquor, dissolving the residue in a fifth solvent, adding a sixth solvent in an amount sufficient to induce precipitation of a solid from a mother liquor containing substantially all of the product, separating the mother liquor from the solid, and isolating the product from the mother liquor.

11. The process of claim 10 wherein the fifth solvent is selected from the group consisting of ethyl acetate, acetone, acetonitrile, methanol, ethanol, 2-propanol, tetrahydrofuran, and N,N-dimethylformamide.

12. The process of claim 10 wherein the sixth solvent is selected from the group consisting of diethyl ether, methyl t-butyl ether, hexane, heptane, octane, and cyclohexane.

13. The process of claim 10 wherein the fifth solvent is ethyl acetate and the sixth solvent is heptane.

14. A process for the isolation of a product containing a compound of formula III comprising:
  (a) evaporating the mixture resulting from reaction of protoporphyrin IX dimethyl ester (PDE) with dimethyl acetylenedicarboxylate (DMAD) to dryness to leave a residue;
  (b) dissolving the residue in toluene;
  (c) mixing the solution from step (b) with between 5 and 10 parts by volume of heptane to induce precipitation of a solid;
  (d) collecting the solid from step (c) by filtration;
  (e) washing the solid from step (d) with a first solvent mixture comprising about 1 part by volume toluene and between 5 and 10 parts by volume of heptane;
  (f) dissolving the solid from step (e) in toluene;
  (g) mixing the solution from step (f) with a second solvent mixture comprising about 1 part by volume toluene and between 3 to 5 parts by volume of heptane to induce precipitation of a solid from a mother liquor containing substantially all of the product;
  (h) separating the mother liquor from step (g) from the solid by filtration;
  (i) Evaporating the mother liquor from step (h) to leave a solid residue;
  (j) Dissolving the solid residue from step (i) in ethyl acetate;
  (k) mixing the solution from step (j) with an amount of a heptane sufficient to induce precipitation of a solid from a mother liquor containing substantially all of the product;
  (l) separating the mother liquor from the solid from step (k) by filtration;
  (m) evaporating the mother liquor from step (l) to give product.

15. The process of claim 14 further comprising washing the solid from step (k) with a mixture comprising about 1 part by volume ethyl acetate and between 3 and 5 parts by volume heptane and combining the washings with the mother liquor from step (m) prior to evaporating the solution to give product.

16. The process of claim 14 further comprising evaporating the ethyl acetate solution from step (j) to dryness and redissolving the residue in ethyl acetate prior to the addition of heptane in step (k).

17. The process of claim 14 wherein step (f) is performed at a temperature of between at 20°–60° C.

18. The process of claim 14 wherein step (f) is performed at a temperature of between at 40°–50° C.

* * * * *

UNITED STATES PATENT AND TRADEMARK OFFICE
CERTIFICATE OF CORRECTION

PATENT NO. : 5,693,789
DATED : December 2, 1997
INVENTOR(S) : Monte et al.

It is certified that error appears in the above-identified patent and that said Letters Patent is hereby corrected as shown below:

Column 8, line 37, change "product" to --said product--.

Signed and Sealed this

Thirty-first Day of March, 1998

Attest:

BRUCE LEHMAN

*Attesting Officer*       *Commissioner of Patents and Trademarks*